United States Patent [19]
Baker et al.

[11] Patent Number: 5,275,594
[45] Date of Patent: Jan. 4, 1994

[54] ANGIOPLASTY SYSTEM HAVING MEANS FOR IDENTIFICATION OF ATHEROSCLEROTIC PLAQUE

[75] Inventors: Glenn S. Baker, Los Angeles, Calif.; Michael G. Dumont, Stratham, N.H.; Michael Madden, Ashby; Norman E. Farr, North Andover, both of Mass.

[73] Assignee: C. R. Bard, Inc., Murray Hill, N.J.

[21] Appl. No.: 611,994

[22] Filed: Nov. 9, 1990

[51] Int. Cl.$^5$ .............................................. A61N 5/06
[52] U.S. Cl. .................................... 606/12; 606/7; 606/10; 606/15; 606/16
[58] Field of Search ............... 128/395, 397, 398, 633; 606/2, 3, 7, 13-

[56] References Cited

U.S. PATENT DOCUMENTS

| | | | |
|---|---|---|---|
| 4,316,467 | 2/1982 | Muckerheid | 128/303.1 |
| 4,336,809 | 1/1982 | Clark | 128/665 |
| 4,543,477 | 9/1985 | Doi et al. | 250/205 |
| 4,556,057 | 12/1985 | Hiruma et al. | 128/303.1 |
| 4,641,650 | 2/1987 | Mok | 128/303.1 |
| 4,682,594 | 7/1987 | Mok | 128/303.1 |
| 4,718,417 | 1/1988 | Kittrell | 128/303.1 |
| 4,785,806 | 11/1988 | Deckelbaum | 128/303.1 |
| 4,800,876 | 1/1989 | Fox et al. | 128/303.1 |
| 4,817,601 | 4/1989 | Roth et al. | 128/303.1 |
| 4,850,351 | 1/1989 | Herman et al. | 604/21 |
| 4,917,084 | 4/1990 | Sinofsky | 128/303.1 |
| 4,939,336 | 7/1990 | Meyer et al. | 219/121.62 |
| 4,950,266 | 8/1990 | Sinofsky | 128/303.1 |

FOREIGN PATENT DOCUMENTS 200390  4/1986  European Pat. Off. .

OTHER PUBLICATIONS

"Acoustic and Plasma-Guided Laser Angioplasty" by Bhatta et al., Lasers in Surg & Med vol. 9 pp. 117-123 (1989).

G. Laufer et al, Lasers in Surgery and Medicine, vol. 9, 1989, pp. 556-571.
R. H. Clark et al, Lasers in Surgery and Medicine, vol. 8, 1988, pp. 45-59.
M. R. Prince et al, IEEE J. Quantum Electronics, vol. QE-23, No. 10, Oct. 1987, pp. 1783-1786.
P. Teng et al, Appl. Phys. B, vol. 42, 1987, pp. 73-78.
G. Laufer et al, Circulation, vol. 78, No. 4, Oct. 1988, pp. 1031-1039.
T. D. Gauthier et al, J. Applied Physics, vol. 64, No. 5, Sep. 1, 1988, pp. 2736-2741.
L. I. Deckelbaum, Lasers in Surgery and Medicine, vol. 7, 1987, pp. 330-335.
R. Brinkmann, "On The Way to The Ideal Lithotripsy Laser", Date Unknown.
K. M. Bhatta et al, Lasers in Surgery and Medicine, vol. 9, 1989, pp. 117-123.

*Primary Examiner*—David M. Shay
*Attorney, Agent, or Firm*—Wolf, Greenfield & Sacks

[57] ABSTRACT

An angioplasty system and method for identification and laser ablation of atherosclerotic plaque at a target site in a blood vessel includes fluorescence analysis for identification of noncalcified plaque and calcium photoemission analysis for identification of calcified plaque. Calcified plaque is identified by time domain analysis of calcium photoemission. A high energy pulsed ultraviolet laser can be used for stimulation of fluorescence and for stimulation of calcium photoemission. The system is capable of distinguishing between calcium photoemission and a defective condition of optical fibers that are used to deliver laser energy to the target site. In an another embodiment of the angioplasty system, calcium photoemission is identified during a nonablative initial portion of the laser ablation pulse. When calcium photoemission is not identified, the laser ablation pulse is terminated during the initial nonablative portion thereof.

4 Claims, 11 Drawing Sheets

ANGIOPLASTY SYSTEM HAVING MEANS FOR IDENTIFICATION OF ATHEROSCLEROTIC PLAQUE

FIELD OF THE INVENTION

This invention relates to methods and apparatus for removal of biological material in blood vessels with laser energy and, more particularly, to systems which distinguish between atherosclerotic plaque and normal tissue by analyzing photoemissions from a target site. When atherosclerotic plaque is identified, laser energy is used to ablate the plaque.

BACKGROUND OF THE INVENTION

Transluminal angioplasty involves the nonsurgical widening of a passage through an artery that has been narrowed, or stenosed, by deposits of plaque or plaque-ridden tissue. One approach to transluminal angioplasty involves the use of laser energy to vaporize, ablate or otherwise remove the plaque deposits. A catheter containing one or more optical fibers is advanced through an artery until its distal end is positioned adjacent to an obstruction. Laser energy sufficient to ablate the obstruction is directed through the optical fibers. A catheter for removal of biological obstructions with laser energy is disclosed in U.S. Pat. No. 4,817,601, issued Apr. 4, 1989 to Roth et al. A laser catheter including multiple optical fibers and adapted to be guided to a target site by a guidewire is disclosed in U.S. Pat. No. 4,850,351, issued Jul. 25, 1989 to Herman et al. Laser catheter systems utilizing infrared wavelengths for tissue issued Apr. 17, 1990 to Sinofsky, and U.S. Pat. No. 4,950,266, issued Aug. 21, 1990 to Sinofsky. Wavelengths in the visible and ultraviolet wavelength ranges have also been utilized for removal of biological material.

When laser energy is used to vaporize or ablate atherosclerotic plaque, thermal damage to surrounding normal tissue is a serious risk. The diameter of arteries is on the order of one to a few millimeters, and the energy level used for ablation of plaque is sufficient to damage or destroy normal tissue. Due to the frequent bends in arteries, the distal end of a laser catheter may be directed at an artery wall rather than at obstructing material. Inadvertent perforation of an artery with laser energy can have serious consequences. The use of pulsed laser energy for tissue ablation, with pulse parameters selected to minimize the risk of thermal damage, is disclosed in U.S. Pat. No. 4,800,876 issued Jan. 31, 1989 to Fox et al.

Since the ablation procedure is performed with a catheter, the tissue being ablated cannot be directly observed. Endoscopic techniques are usually impractical, since the fiber optics for illumination and viewing would increase the diameter of the catheter and reduce its flexibility to an unacceptable degree. Fluoroscopic techniques permit the location of the catheter to be determined, but do not identify the type of tissue being removed.

Techniques have been proposed for distinguishing between plaque and normal tissue by stimulating fluorescence from tissue in an artery and analyzing the frequency spectrum of the fluorescence. U.S. Pat. No. 4,785,806, issued Nov. 22, 1988 to Deckelbaum, discloses the use of ultraviolet laser energy for stimulating fluorescence. Fluorescence intensity at selected wavelengths in the blue/green wavelength range is analyzed to distinguish between plaque and normal tissue. The use of a dye to enhance the contrast between the fluorescence from plaque and the fluorescence from normal tissue is disclosed in U.S. Pat. No. 4,641,650, issued Feb. 10, 1987 to Mok. The use of visible light to stimulate fluorescence from atherosclerotic plaque is disclosed in U.S. Pat. No. 4,718,417, issued Jan. 12, 1988 to Kittrell et al.

It has been recognized that atherosclerotic plaque may have different characteristics, depending on a variety of factors. In particular, calcified plaque is relatively dense and requires more energy for ablation, whereas noncalcified plaque is softer and is more easily removed. G. Laufer et al in *Lasers in Surgery and Medicine*, Vol. 9, 1989, pages 556–571, describe application of 308 nanometer excimer laser energy to various types of arterial tissue, including normal arterial tissue, fibrous plaque, lipid plaque and calcified plaque. The spectral emission from the tissue was studied. Laufer et al state that calcified plaque exhibits a spectral line shape that is quite different from that of uncalcified arterial tissue. The feasibility of spectroscopic target tissue characterization and a real time spectroscopically-guided device are suggested.

R. H. Clark et al in *Lasers in Surgery and Medicine*, Vol. 8, 1988, pages 45–59, describe research on laser spectroscopic measurements of cardiovascular tissue including laser Raman light scattering, laser-induced plasma photoemission, laser-induced fluorescence and photoinduced electron paramagnetic resonance. The photoemission from calcified coronary arteries is discussed. The authors suggest that the measurements can serve as monitors during the course of laser photoablation.

M. R. Prince et al in *IEEE Journal of Quantum Electronics*, Vol. QE-23, No. 10, October 1987, pages 1783–1786, describe the differences between laser ablation of calcified plaque and noncalcified plaque. The authors believe that a laser induced plasma creates a shock wave that assists in ablation of the calcified plaque.

P. Teng et al in *Appl. Phys.* B, Vol. 42, pages 73–78, 1987 describe studies of laser fragmentation of biliary calculi. The temporal and spectral characteristics of the flash of light accompanying fragmentation of gallstones were studied. Formation of a plasma is suggested.

It is desirable to provide an angioplasty system which is capable of accurately identifying and ablating both calcified and noncalcified atherosclerotic plaque. The system should minimize the risk of damage or perforation of normal arterial tissue.

It is a general object of the present invention to provide improved methods and apparatus for angioplasty.

It is another object of the present invention to provide methods and apparatus for identifying and ablating calcified and noncalcified atherosclerotic plaque.

It is a further object of the present invention to provide methods and apparatus for determining the presence of calcified plaque at a target site in a blood vessel by analyzing a time domain signal representative of calcium photoemission from tissue at the target site.

It is a further object of the present invention to provide methods and apparatus for identification of atherosclerotic plaque at a target site in a blood vessel utilizing analysis of fluorescence by noncalcified plaque and analysis of calcium photoemission by calcified plaque.

It is yet another object of the present invention to provide methods and apparatus for distinguishing between photoemission from calcified plaque and photoemission from a damaged optical fiber.

SUMMARY OF THE INVENTION

According to the present invention, these and other objects and advantages are achieved in an angioplasty system and method. The angioplasty system comprises a source of laser energy for stimulation of fluorescence by noncalcified atherosclerotic plaque at a target site in a blood vessel, a source of laser energy for stimulation of photoemission by calcified atherosclerotic plaque at the target site, a source of high power laser energy for ablation of atherosclerotic plaque at the target site, a laser catheter for delivering the laser energy to the target site, first analyzing means for determining whether a spectrum of the fluorescence emitted by tissue at the target site is representative of noncalcified atherosclerotic plaque, second analyzing means for determining whether photoemission by tissue at the target site is representative of calcified atherosclerotic plaque, and means for enabling the source of high power laser energy to direct high power laser energy at the target site if the first analyzing means or the second analyzing means indicates the presence of atherosclerotic plaque.

By analyzing the frequency spectrum of fluorescence emitted from noncalcified plaque and calcium photoemission from calcified plaque, the system reliably identifies and ablates atherosclerotic plaque. The angioplasty system is typically implemented with two lasers. In one preferred embodiment of the angioplasty system, a diagnostic laser stimulates fluorescence by noncalcified plaque, and a high power ablation laser stimulates calcium photoemission by calcified plaque and also performs ablation of tissue. In a second preferred embodiment, a high peak power pulsed ultraviolet diagnostic laser stimulates fluorescence by noncalcified plaque and stimulates calcium photoemission by calcified plaque. A high power ablation laser is energized only after plaque is identified at the target site.

The second analyzing means for determining whether calcium photoemission is representative of calcified plaque preferably includes means for analyzing a time domain signal representative of calcium photoemission. The means for analyzing a time domain signal can include means for determining that 1) the area under all or a portion of the time domain signal, 2) the amplitude of the time domain signal at one or more times, or 3) the decay rate of all or a portion of the time domain signal meets a predetermined criteria. When the predetermined criteria is satisfied, the presence of calcified plaque is indicated. In a preferred embodiment, calcified plaque is indicated when the area under the time domain signal exceeds a predetermined value.

In a preferred embodiment, the angioplasty system further includes means for detecting a defective condition of one or more optical fibers in the laser catheter. The defective region of the optical fiber transmits optical energy through the laser catheter in a reverse direction. The optical energy appears as a photoemission in response to a laser pulse. The means for detecting a defective condition of the optical fibers includes means for measuring the area under a time domain signal representative of the photoemission, the measurement beginning a predetermined time after the start of the laser pulse, and means for indicating a defective condition of the optical fibers when the area exceeds a predetermined value. The angioplasty system analyzes the time domain signal to distinguish between calcium photoemission from calcified plaque and a defective catheter condition. When a defective catheter condition is identified, the procedure is terminated.

According to another aspect of the invention, there is provided methods and apparatus for distinguishing between calcified atherosclerotic plaque and tissue which does not contain calcified atherosclerotic plaque. The apparatus comprises a source of laser energy for stimulation of photoemission by calcified atherosclerotic plaque at a target site in a blood vessel, a laser catheter for delivering laser energy from the source to the target site, and means for analyzing a time domain signal responsive to photoemission by tissue at the target site and determining whether the time domain signal is representative of calcified atherosclerotic plaque or tissue which does not contain calcified atherosclerotic plaque.

An angioplasty system in accordance with a further aspect of the present invention comprises a source of laser pulses for ablation of tissue and for stimulation of photoemission by calcified atherosclerotic plaque at a target site in a blood vessel, each of the laser pulses including a nonablative initial portion, a laser catheter for delivering the laser pulses from the source to the target site, analyzing means for determining whether a time domain signal responsive to photoemission by tissue at the target site is representative of calcified atherosclerotic plaque or tissue which does not contain calcified atherosclerotic plaque, and means for terminating each of the laser pulses during the nonablative initial portion thereof if the time domain signal is not representative of calcified atherosclerotic plaque. By terminating the laser pulse during the nonablative initial portion thereof ablation of normal tissue is avoided.

BRIEF DESCRIPTION OF THE DRAWINGS

For a better understanding of the present invention, together with other and further objects, advantages and capabilities thereof, reference is made to the accompanying drawings which are incorporated herein by reference and in which.

DETAILED DESCRIPTION OF THE INVENTION

Figure 1:
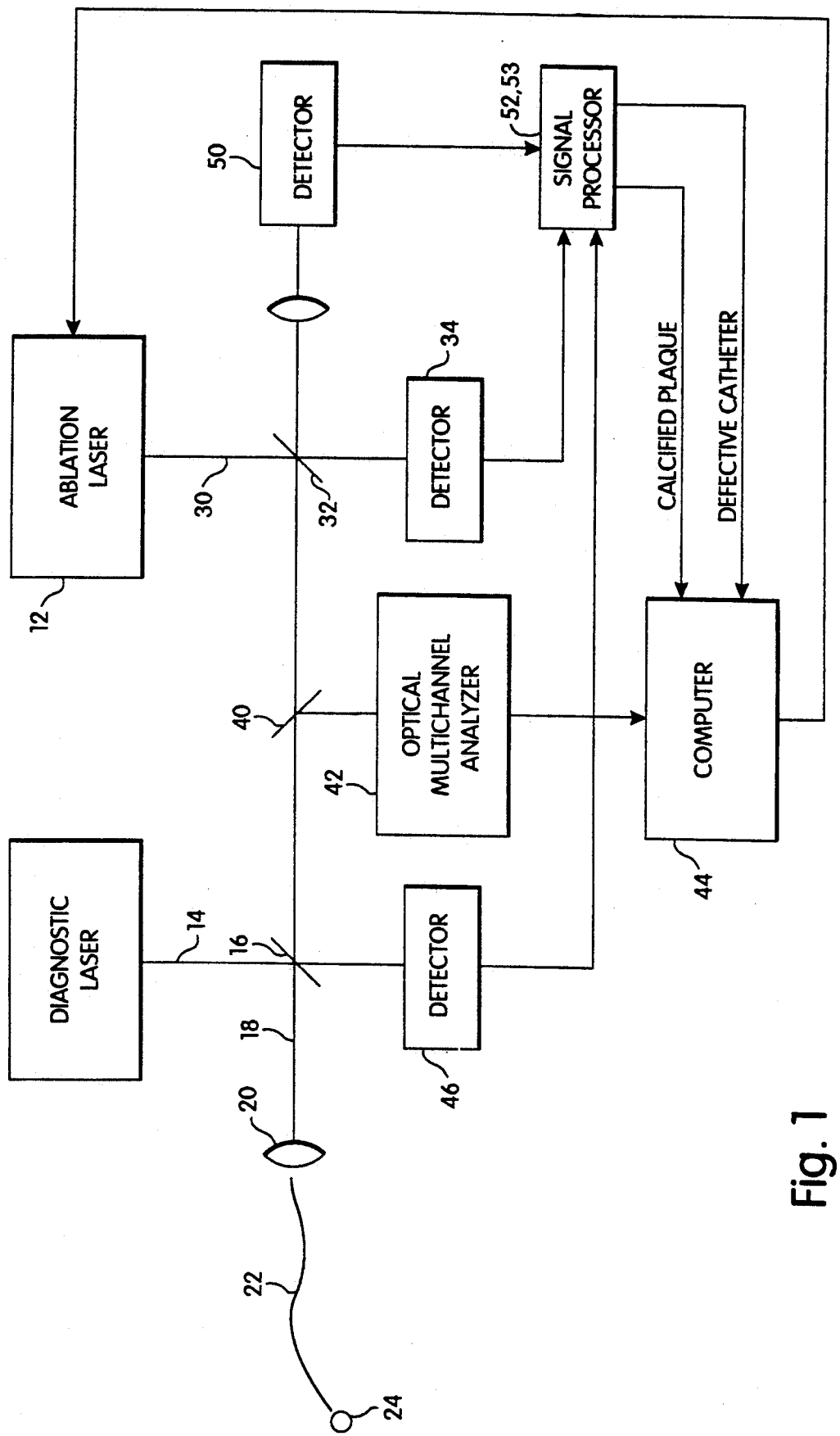
FIG. 1 is a schematic block diagram of an angioplasty system in accordance with the present invention.

A block diagram of an angioplasty system for identification and ablation of atherosclerotic plaque is shown in FIG. 1. The system is typically used for ablation of plaque in arteries such as coronary arteries. The system includes a source of laser energy for stimulation of photoemission by calcified atherosclerotic plaque at a target site in a blood vessel, a source of laser energy for stimulation of fluorescence by noncalcified atherosclerotic plaque at the target site and a source of high power laser energy for ablation of tissue at the target site. In most cases, the system can be implemented with two lasers. The system of FIG. 1 includes a diagnostic laser 10 for stimulation of fluorescence by noncalcified plaque and an ablation laser 12 for ablation of tissue at the target site. In one embodiment of the angioplasty system, the ablation laser 12 is also a source of laser energy for stimulation of photoemission by calcified plaque. In another embodiment of the angioplasty system, the diagnostic laser 10 is also a source of laser energy for stimulation of photoemission by calcified plaque. Both embodiments are described in detail hereinafter.

An output laser beam 14 from diagnostic laser 10 is directed by a beam splitter 16 along an optical path 18 and through a lens 20 to the proximal end of a laser catheter 22. The laser catheter 22 contains one or more optical fibers which transmit laser energy to the distal end of the catheter 22. The laser catheter 22 is advanced through an artery until its distal end is positioned adjacent to an obstruction 24. The obstruction is typically atherosclerotic plaque, which may be calcified, noncalcified, or a combination thereof. Laser energy from diagnostic laser 10 is directed by the optical system and the laser catheter 22 to the obstruction 24. Suitable laser catheters are disclosed in U.S. Pat. Nos. 4,850,351 and 4,817,601, which are hereby incorporated by reference. Optical energy can also be carried to and from the target site through a guidewire having one or more optical fibers for transmission of optical energy. As used herein, the term "laser catheter" refers to any catheter, guidewire or other device capable of transluminal delivery of optical energy.

An output laser beam 30 of ablation laser 12 is directed along optical path 18 by a beam splitter 32. The laser beam 30 is directed to obstruction laser 24 by the laser catheter 22. A portion of the laser beam 30 passes through beam splitter 32 and impinges on a photodetector 34.

The diagnostic laser 10 is selected to stimulate fluorescence from atherosclerotic plaque at the target site. In a first preferred embodiment of the angioplasty system, the diagnostic laser 10 has a continuous output in the ultraviolet wavelength range. An example of such a laser is a helium-cadmium laser having a wavelength of 325 nanometers. The required minimum power density of the laser energy at the target site is on the order of 50 microwatts per square millimeter.

Fluorescence emitted by obstruction 24 is transmitted through laser catheter 22 to the optical system and is directed by a beam splitter 40 to an optical multichannel analyzer 42. The optical multichannel analyzer 42 separates the fluorescence from obstruction 24 into its component wavelengths and determines the intensity of each component wavelength. This spectral information regarding the fluorescence is provided to a computer 44. The computer 44 can be any general purpose digital computer. The computer 44 analyzes the spectral information contained in the fluorescence and identifies the obstruction 24 as atherosclerotic plaque or normal tissue. Further details regarding the identification of plaque by spectral analysis of fluorescence stimulated by ultraviolet laser energy is disclosed in U.S. Pat. No. 4,785,806. Spectral analysis of fluorescence stimulated by visible laser energy is disclosed in U.S. Pat. No. 4,718,417. The disclosures of U.S. Pat. Nos. 4,785,806 and 4,718,417 are hereby incorporated by reference. When the diagnostic laser 10 is an ultraviolet laser, the fluorescence analysis technique disclosed in U.S. Pat. No. 4,785,806 can be utilized for distinguishing between plaque and normal tissue.

It has been discovered that the analysis of fluorescence is capable of identifying noncalcified plaque but is not capable of reliably identifying calcified plaque. Thus, a negative result from the fluorescence analysis may indicate the presence of normal tissue or the presence of calcified plaque. When the fluorescence analysis is used to control activation of the ablation laser, a negative result may cause a failure to ablate calcified plaque. Since it is desired to ablate both noncalcified plaque and calcified plaque, the fluorescence analysis technique is inadequate when used alone.

It is known that when laser energy is applied to calcified plaque, photoemission occurs. The photoemission has a spectrum which is different from the spectrum of fluorescence from noncalcified plaque. The spectrum of the photoemission from calcified plaque indicates the presence of calcium. The photoemission from calcified plaque is believed to have characteristics of a plasma emission. We have discovered that calcified plaque can be reliably identified by analysis of a time domain signal which represents the photoemission from calcified plaque. The photoemission from calcified plaque stimulated by a laser pulse is characterized by a broadband pulse of high intensity and short duration. In one example, photoemission from calcified plaque was stimulated by a pulse from a holmium-doped YAG laser having a wavelength of 2.1 micrometers, a pulse duration of 300–400 microseconds and an energy density at the target site of about 1–2 Joules per square millimeter. The photoemission from calcified plaque under these conditions has been observed to have a pulse width of about 10–100 microseconds.

In the first embodiment of the angioplasty system, wherein the diagnostic laser 10 is a low power continuous wave ultraviolet laser, photoemission from calcified plaque is stimulated by a single pulse of the ablation laser 12. The photoemission stimulated by ablation laser 12 is transmitted by laser catheter 22 from obstruction 24 to the optical system. The photoemission is directed along optical path 18 to a photodetector 50. The detector 50, which has a broadband optical response, receives the photoemission from the target site and generates a time domain signal. The output of detector 50 is connected to an input of a signal processor 52. The output of detector 34 is also connected to an input of signal processor 52. Calcified plaque and defective catheter signals from the output of signal processor 52 are connected to the computer 44. A detector 46 shown in FIG. 1 is not used in the first embodiment of the angioplasty system wherein the diagnostic laser 10 is a low power continuous wave ultraviolet laser.

The ablation laser 12 is preferably a pulsed laser having an output wavelength in the range of about 1.8 to 2.2 micrometers. Preferred lasers include holmium-doped yttrium aluminum garnet (YAG), holmium-doped yttrium lithium fluoride (YLF), thulium-doped YAG and thulium-doped YLF. Further details regarding these and other suitable lasers are disclosed in U.S. Pat. Nos. 4,950,266 and 4,917,084, which are hereby incorporated by reference. The optical multichannel analyzer 42 can be a type SA, CP200, manufactured by Princeton Instruments. The detector 34 can be an indium arsenide detector, and the detector 50 can be a silicon photovoltaic detector which is sensitive to a broad band of wavelengths in the near infrared range, typically 800 nanometers to 1.2 micrometers.

Figure 2:
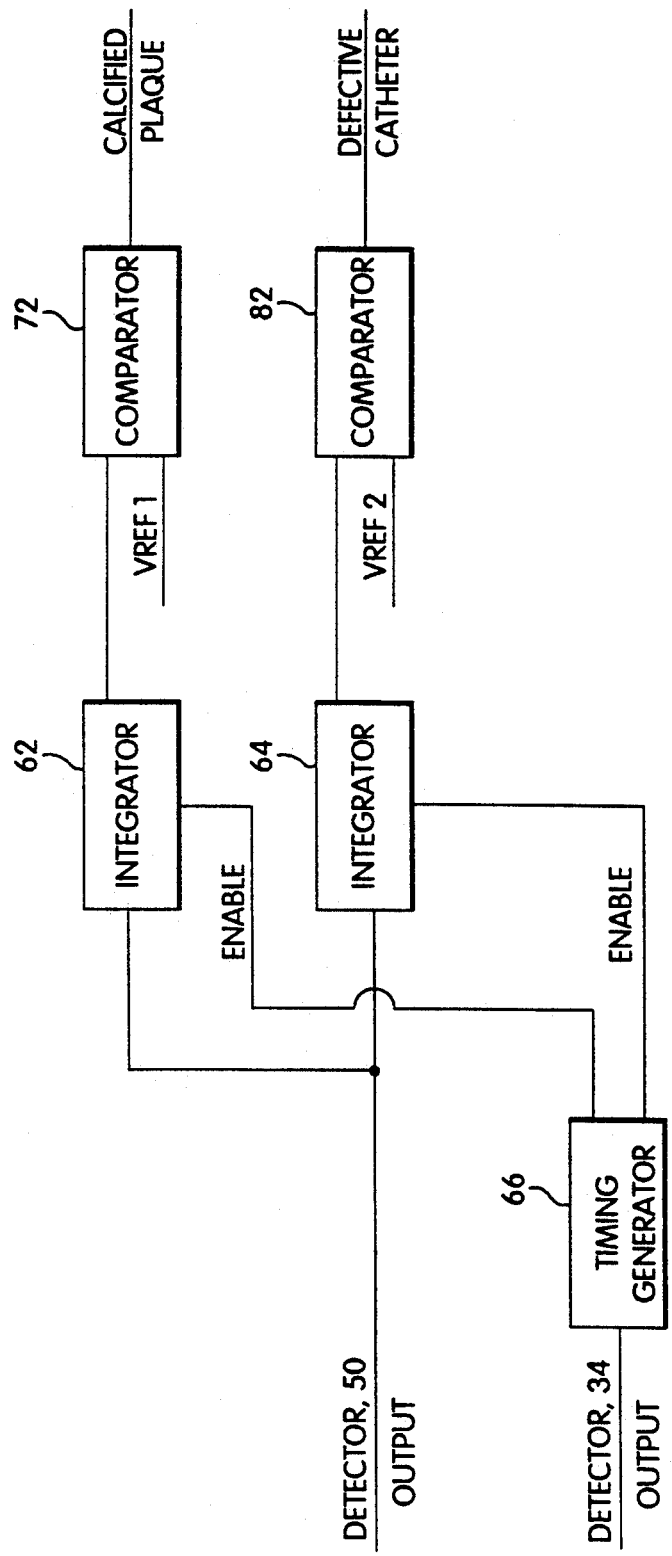
FIG. 2 is a schematic block diagram of the signal processor shown in FIG. 1 in accordance with a first embodiment of the angioplasty system.
Figure 3:
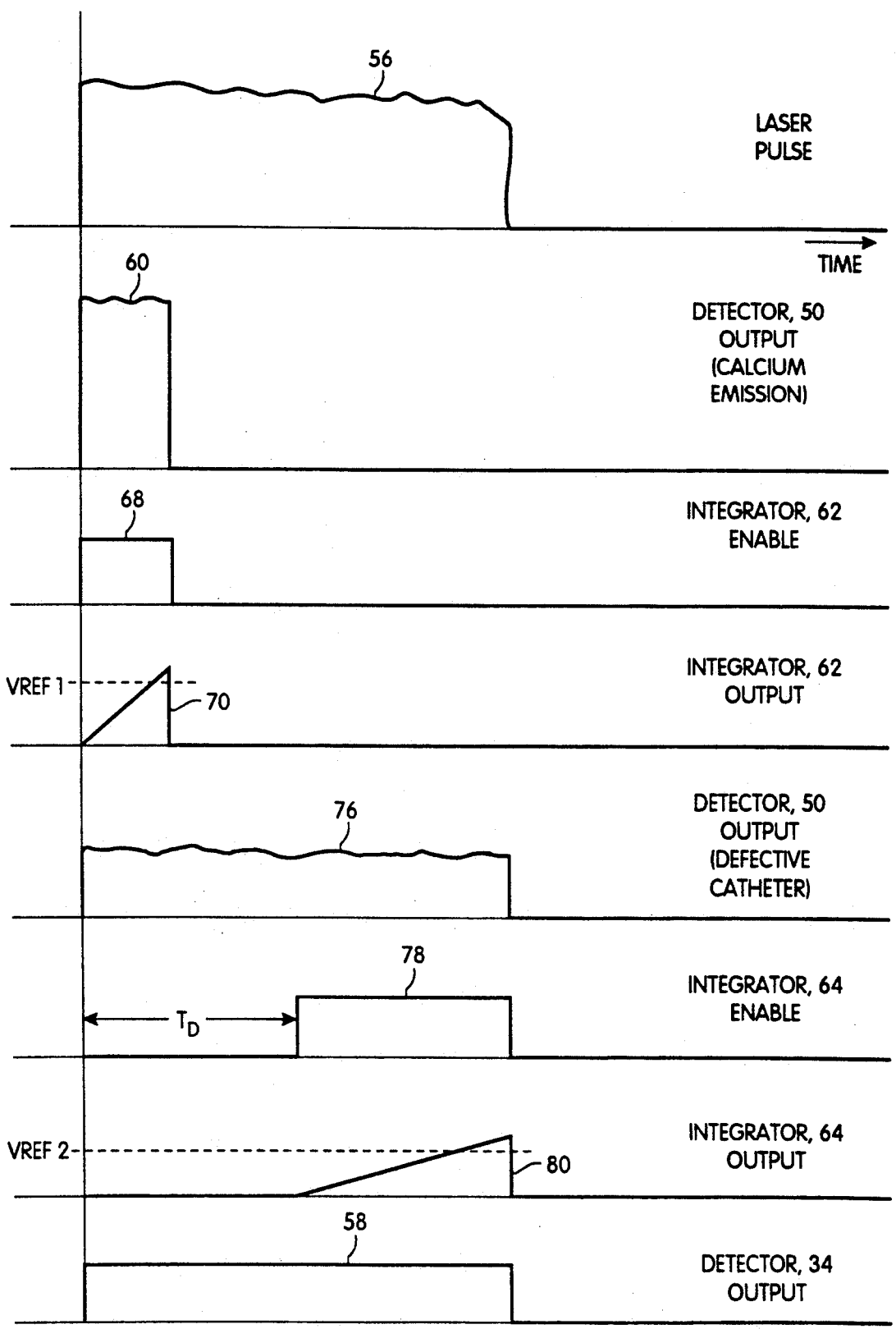
FIG. 3 is a timing diagram which shows waveforms in the first embodiment of the angioplasty system shown in FIG. 1.

A block diagram of the signal processor 52 for the first embodiment of the angioplasty system is shown in FIG. 2. Waveforms associated with the signal processor 52 are shown in FIG. 3. The signal processor 52 performs an analysis of a time domain signal provided by detector 50 and generates signals which indicate the presence of calcified plaque or a defective condition of the laser catheter 22. In order to stimulate photoemission from calcified plaque at the target site, the ablation laser 12 generates a laser pulse 56 as shown in FIG. 3. For a holmium-doped YAG ablation laser, the pulse duration is on the order of 300–400 microseconds. The detector 34 receives a portion of laser pulse 56 and generates a timing pulse 58 which identifies the start of the laser pulse.

When calcified plaque is present at the target site, a high intensity, short duration calcium emission pulse is received by detector 50. The corresponding time domain signal 60 at the output of detector 50 is shown in FIG. 3. Referring again to FIG. 2, the output of detector 50 is connected to the input of an integrator 62 and to the input of an integrator 64. The output of detector 34 is connected to the input of a timing generator 66. The timing generator 66 provides enable signals to each of the integrators 62 and 64. The integrators 62 and 64 can be conventional operational amplifier integrators wherein the input signal charges a capacitor during the period that the integrator is enabled. The integrators 62 and 64 determine the area under the time domain signal from detector 50 during the time when each integrator is enabled. As indicated above, the calcium emission signal 60 has a duration on the order of 10–100 microseconds and is shorter in duration than the laser pulse 56. The timing generator 66 generates an enable signal 68 for integrator 62 of approximately 10-100 microseconds. The output of integrator 62, as indicated by waveform 70 in FIG. 3, is connected to one input of a comparator 72. A reference voltage VREF1 is connected to the other input of comparator 72. When the output of integrator 62 exceeds the reference voltage VREF1, the comparator 72 provides an output signal, typically a digital change of state, indicative of the presence of calcified plaque at the target site. When the output of integrator 62 remains below the reference voltage VREF1, a calcified plaque signal is not generated by comparator 72. The calcified plaque signal is suppled to computer 44. Thus, the presence of calcified plaque is determined by a relatively simple analysis of the time domain signal which represents calcium emission.

The integrator 62 measures the area under the calcium emission signal 60, and the comparator 72 compares the measured area with a reference value. The peak value of waveform 70 at the output of integrator 62 increases as the area under calcium emission signal 60 increases. The area under all or a portion of the calcium emission signal 60 can be determined. When the area under a portion of the calcium emission signal 60 is to be measured, the integrator enable signal 68 is shortened in duration. When the area under all of the calcium emission signal 60 is to be measured, the integrator enable signal 68 is made equal to or longer than the expected duration of the calcium emission signal. Thus, the area under the time domain signal is measured by integrating the time domain signal for a prescribed interval determined by the integrator enable signal.

The time domain signal can also be analyzed by measuring its amplitude at one or more predetermined times relative to the start of the laser pulse. The amplitude values are compared with reference values to determine the presence of calcified plaque. In still another technique for analyzing the time domain signal representative of calcium emission, the decay rate of all or a portion of the time domain signal is measured. The presence of calcified plaque is determined by comparison of the measured decay rate with a reference value. Techniques for measurement of amplitude and decay rate of a time domain signal are well known in the art.

The optical fiber or fibers in laser catheter 22 are subject to damage during operation. The distal ends of the optical fibers may be burned during the delivery of high energy laser pulses to a target site. When such damage occurs, the optical fibers are no longer effective in delivering laser energy to the target site, and the angioplasty procedure must be terminated. When laser energy is transmitted through damaged optical fibers, energy in the infrared wavelength range is transmitted from the damaged region in a reverse direction toward the laser. A technique for identifying damaged fibers by detecting the energy that is transmitted in a reverse direction is disclosed in U.S. Pat. No. 4,543,477, issued Sep. 24, 1985 to Doi et al.

It has been found that the emission from a defective catheter is lower in intensity and longer in duration than the emission from calcified plaque. The output of detector 50 in the case of a defective catheter is illustrated in FIG. 3 as waveform 76. The signal processor 52 distinguishes between calcium emission and a defective catheter. The distinction is based on the difference in the characteristic waveforms of calcium emission (waveform 60) and defective catheter emission (waveform 76). The defective catheter emission signal continues for the duration of the laser pulse 56, whereas the calcium emission signal has a duration shorter than the laser pulse.

As shown in FIG. 3, the timing generator 66 provides to integrator 64 an enable signal 78 which begins a predetermined time $T_D$ after the start of laser pulse 56 and ends at the same time as the laser pulse. The output of integrator 64, as indicated by waveform 80, is connected to one input of a comparator 82. A reference voltage VREF2 is connected to the other input of comparator 82. When the output of detector 50 represents a defective catheter emission, the output of integrator 64 exceeds reference voltage VREF2, and the comparator 82 provides a defective catheter signal.

The integrator 64 and the comparator 82 thus measure the area under the defective catheter emission, as indicated by waveform 76, and compare the measured area with a reference value. Alternatively, one of the other techniques described above for analyzing the time domain signal representative of calcium emission can be utilized for analyzing the defective catheter emission.

Since the waveform 60 representative of calcium emission ends before integrator 64 is enabled, the integrator 64 provides little or no output in the case of calcium emission, and the reference voltage VREF2 is not exceeded. Therefore, a defective catheter condition is not indicated by comparator 82 when a calcium emission signal is received. The delay $T_D$ between the start of laser pulse 56 and the start of the enable signal 64 is typically on the order of about 250 microseconds. However, it will be understood that the delay $T_D$ is selected depending on the relative lengths of the laser pulse 56 and the calcium emission signal 60. The integrator 64 is typically enabled after most or all of the longest expected calcium emission has ended.

The defective catheter emission signal 76 is integrated by integrator 62 during enable signal 68. Since the defective catheter emission signal 76 is substantially lower in amplitude than the calcium emission signal 60, the output of integrator 62 remains below the reference voltage VREF1, and a calcified plaque signal is not provided by comparator 72 in the case of a defective catheter. Thus, the signal processor shown in FIG. 2 and described above effectively distinguishes between the following conditions: 1) calcified plaque present at the target site, 2) normal tissue or noncalcified plaque present at the target site, and 3) defective catheter. The fluorescence analysis described above distinguishes between noncalcified plaque and normal tissue. Thus, the angioplasty system of FIG. 1 is capable of a four way discrimination.

Figure 4:
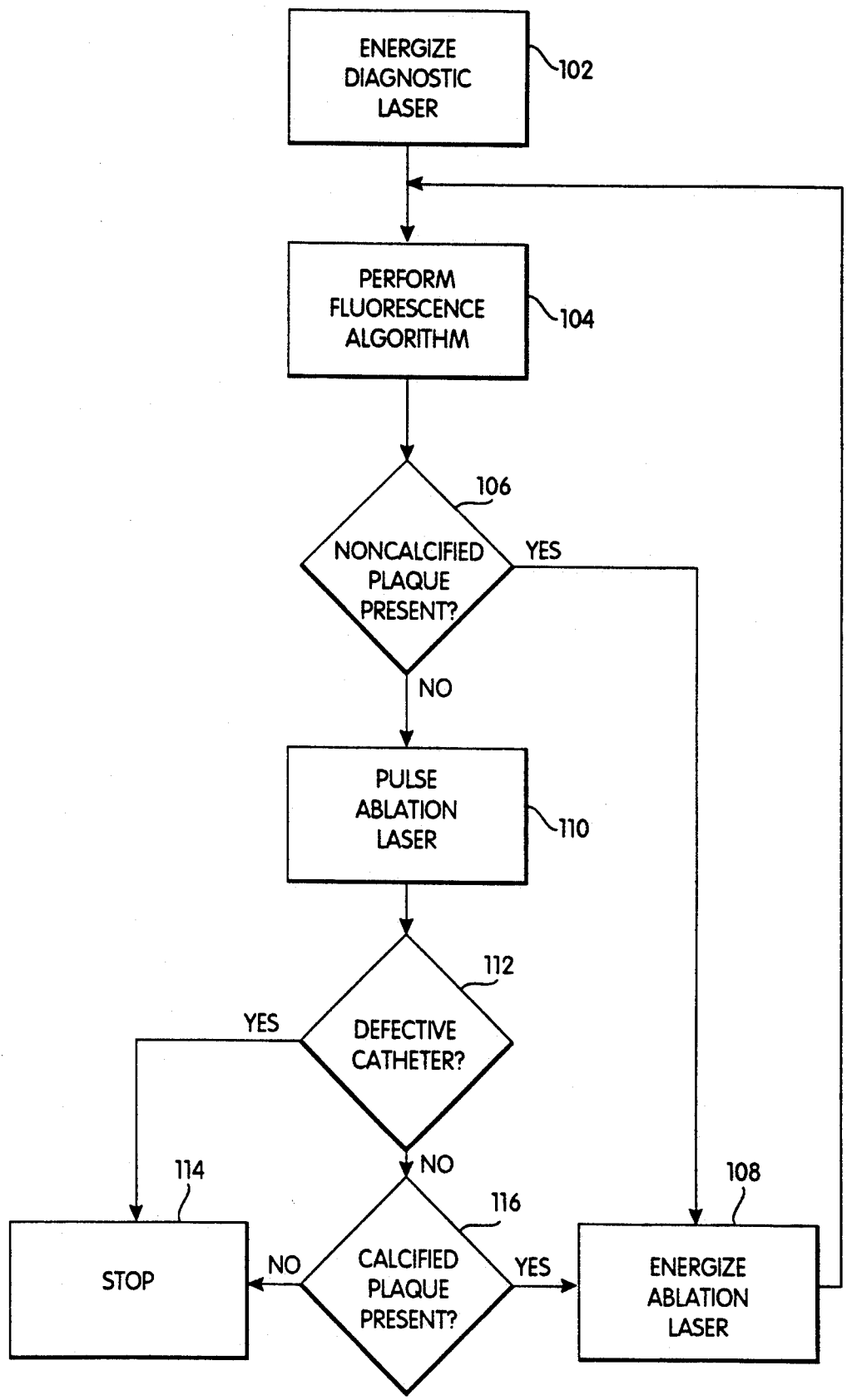
FIG. 4 is a flow diagram which illustrates operation of the first embodiment of the angioplasty system shown in FIG. 1.

Operation of the first embodiment of the angioplasty system is illustrated in the flow chart of FIG. 4. Initially, the diagnostic laser 10 is energized in step 102, and the laser energy from the diagnostic laser is directed to the target site by laser catheter 22. The fluorescence emitted by tissue at the target site is directed by laser catheter 22 and beam splitter 40 to optical multichannel analyzer 42. The spectral information from analyzer 42 is input to computer 44. The computer 44 in step 104 analyzes the spectrum of fluorescence in accordance with the technique described in U.S. Pat. No. 4,785,806.

When the fluorescence analysis indicates the presence of noncalcified plaque in step 106, the ablation laser 12 is energized in step 108 to perform ablation of the noncalcified plaque at the target site. When the fluorescence analysis does not indicate the presence of noncalcified plaque in step 106, the ablation laser 12 is activated in step 110 to transmit a single laser pulse to the target site for stimulation of photoemission by calcified plaque.

The calcium photoemission, if any, from the target site is transmitted through laser catheter 22 to detector 50. The calcium photoemission is analyzed by the signal processor 52 as described above. If the photoemission indicates a defective catheter condition in step 112, the procedure is terminated in step 114. If a defective catheter is not indicated in step 112 and calcified plaque is not indicated as being present in step 116, the procedure is also terminated. In this case, the fluorescence analysis has provided a negative result with respect to noncalcified plaque, and the photoemission analysis has provided a negative result with respect to calcified plaque. If calcified plaque is indicated as being present in step 116, the ablation laser is energized in step 108. Although not shown in FIG. 4, the energizing of the ablation laser in step 108 may result in detection of a defective catheter. In this case, the procedure is terminated.

The ablation laser 12 can be energized either manually or automatically. When manual operation is utilized, the computer provides a visual or audible indication to the surgeon that plaque is present and ablation can proceed. The surgeon then activates the ablation laser 12 manually. The ablation laser 12 can be programmed to provide a single laser pulse or a predetermined number of laser pulses for each manual activation. In the case of automatic activation, the computer 44 provides an activation signal to ablation laser 12. In response to the activation signal, the ablation laser 12 generates a predetermined number of laser pulses for ablation of plaque at the target site. In the case where the laser catheter includes multiple optical fibers, activation of the ablation laser in response to an indication of atherosclerotic plaque can be performed sequentially for each of the optical fibers.

After activation of the ablation laser 12 and ablation of plaque at the target site, the analysis steps are repeated to determine if additional plaque remains at the target site. When a negative result is obtained, the laser catheter 22 can be moved to a different target site, and the procedure can be repeated. Thus, the angioplasty system of the invention progressively ablates both calcified plaque and noncalcified plaque.

In a second preferred embodiment of the angioplasty system shown in FIG. 1, the diagnostic laser 10 stimulates fluorescence from noncalcified plaque at the target site and also stimulates photoemission by calcified plaque at the target site. In this case, the diagnostic laser 10 is a high peak power pulsed laser having an output in the ultraviolet wavelength range. A preferred diagnostic laser in this embodiment is a pulsed nitrogen laser having an output wavelength of 337 nanometers and a pulse duration on the order of 100 nanoseconds. The ablation laser 12 can be any laser having parameters selected to perform ablation of atherosclerotic plaque. Preferred ablation lasers having output wavelengths in the range of about 1.8 to 2.2 micrometers are discussed above in connection with the first embodiment of the angioplasty system. In this embodiment, the ablation laser 12 is not energized until plaque is identified at the target site.

Figure 5:
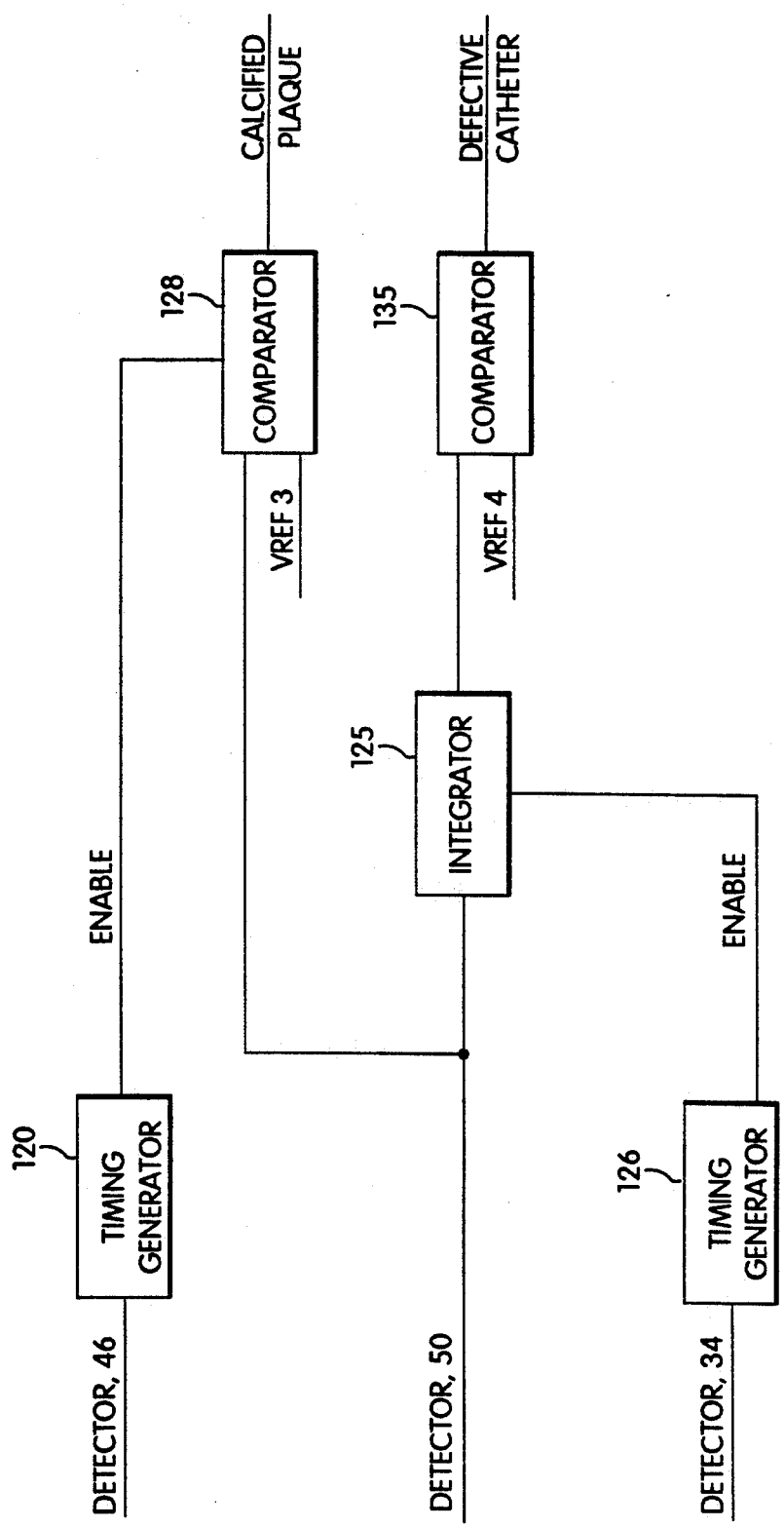
FIG. 5 is a schematic block diagram of the signal processor shown in FIG. 1 in accordance with a second embodiment of the angioplasty system.
Figure 6A:
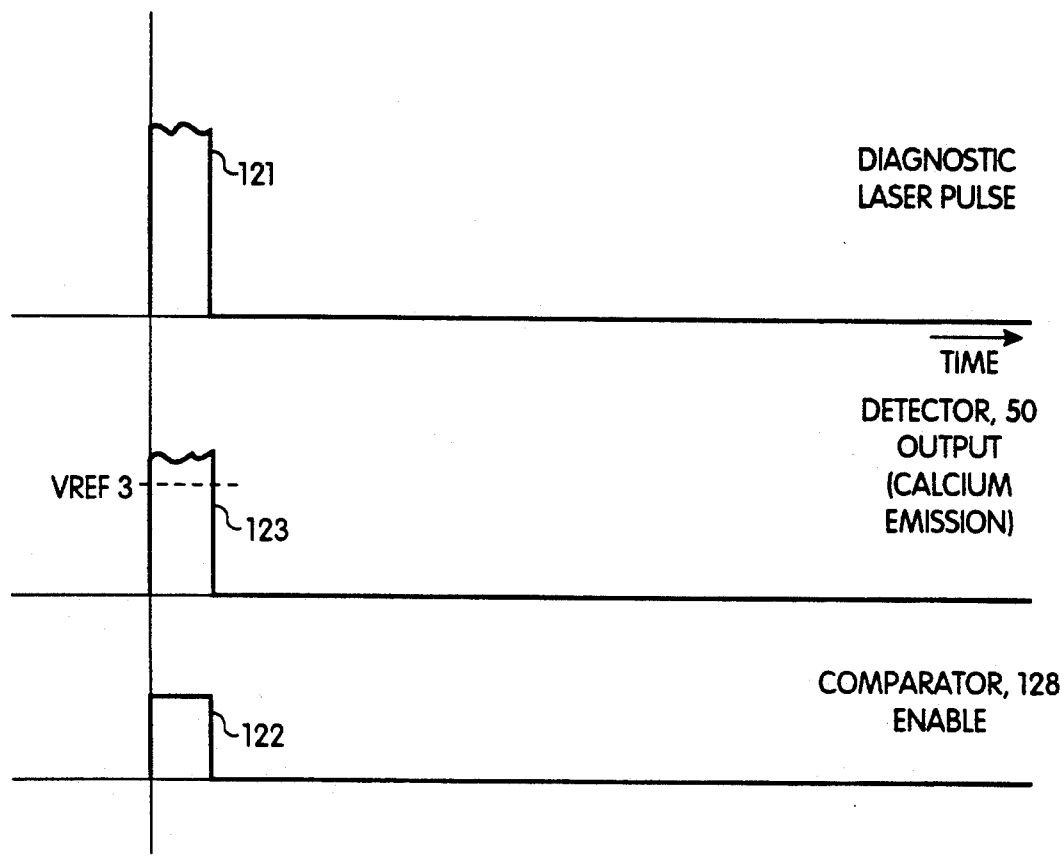
FIGS. 6A and 6B are timing diagrams which show waveforms in the second embodiment of the angioplasty system shown in FIG. 1.
Figure 6B:
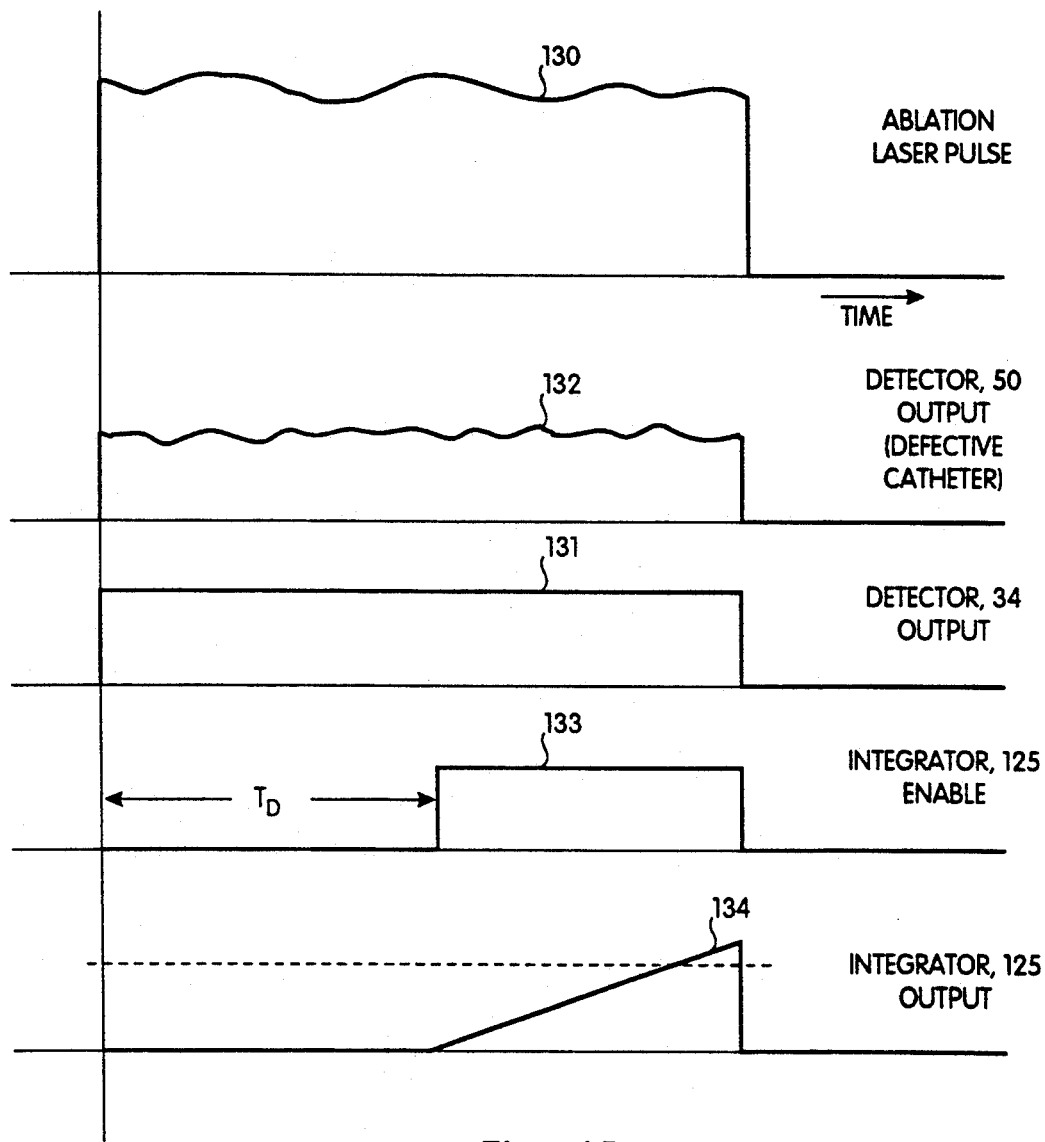

In the second embodiment, the output beam 14 of the high peak power pulsed diagnostic laser 10 is directed by the beam splitter 16 through laser catheter 22, and a portion of the laser beam 14 passes through beam splitter 16 and impinges on photodetector 46. The output of photodetector 46 is connected to one input of signal processor 53. The outputs of detectors 34 and 50 are also connected to signal processor 53. A block diagram of signal processor 53 for the second embodiment of the angioplasty system is shown in FIG. 5. Waveforms associated with signal processor 53 are shown in FIGS. 6A and 6B. The signal processor 53 performs an analysis of time domain signals generated by detector 50 in response to received optical energy and generates signals which indicate the presence of calcified plaque or a defective condition of the laser catheter 22.

As shown in FIG. 5, the output of detector 46 is connected to a timing generator 120. The detector 46 detects a laser pulse 121 from diagnostic laser 10 and causes timing generator 120 to generate a comparator enable signal 122. When calcified plaque is present at the target site, a calcium emission signal 123 is provided by detector 50 in response to a calcium emission. The output of detector 50 is connected to one input of a comparator 128. The comparator enable signal 122 enables comparator 128 during the pulse 121 from diagnostic laser 10. A reference voltage, VREF3 is connected to the other input of comparator 128. When the calcium emission signal 123 exceeds the reference voltage VREF3, the comparator 128 provides an output signal indicative of the presence of calcified plaque at the target site. The calcified plaque signal is supplied to computer 44.

In the second embodiment of the angioplasty system, a defective catheter condition is detected at a different time from the calcium emission. The calcium emission is stimulated and measured as described above in response to pulses from the diagnostic laser 10. A defective catheter condition is detected in response to activation of the ablation laser 12 as shown in FIG. 6B. It should be understood that the events illustrated in FIG. 6B occur at different times than the events illustrated in FIG. 6A, since the ablation laser 12 is activated after the diagnostic laser 10. When atherosclerotic plaque detected at the target site, the ablation laser 12 is activated, and an ablation laser pulse 130 is generated. Although the laser pulse 130 stimulates calcium emission from the target site, the calcium emission is not detected at this time. The detector 34 receives the laser pulse 130 and provides a timing signal 131 to a timing generator 126. In the event of a defective catheter, the detector 50 provides an output signal 132 as shown in FIG. 6B. As described above, the defective catheter signal 132 has a relatively low intensity and a duration approximately equal to that of the laser pulse 130. The output of detector 50 is connected to the input of an integrator 125. The timing generator 126 generates an integrator enable signal 133 which is delayed by a predetermined time delay $T_D$ relative to the start of laser pulse 130. Thus, the integrator 125 is enabled during the latter portion of laser pulse 130. The output of integrator 125 as indicated by waveform 134 in FIG. 6B, is connected to one input of a comparator 135. A reference voltage VREF4 is connected to the other input of comparator 135. When the output of detector 50 represents a defective catheter emission, the output of integrator 125 exceeds reference voltage VREF4, and the comparator 135 provides a defective catheter signal to computer 44. The time delay $T_D$ associated with the integrator enable signal 133 permits the signal processor to distinguish between a defective catheter condition and a calcium emission, as described above in connection with the first embodiment of the angioplasty system.

Figure 7:
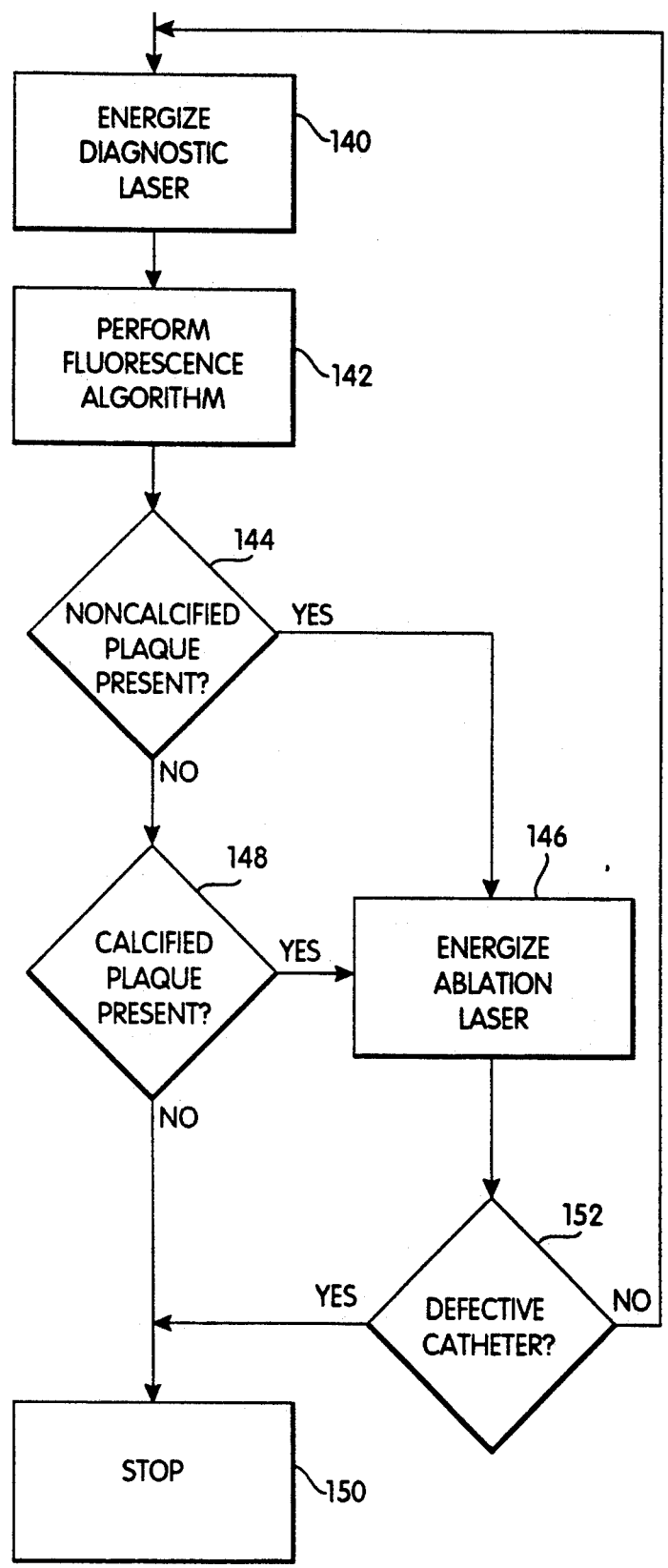
FIG. 7 is a flow diagram which illustrates operation of the second embodiment of the angioplasty system shown in FIG. 1.

Operation of the second embodiment is illustrated in the flow chart of FIG. 7. The diagnostic laser 10 is energized in step 140 to cause a high peak power pulse of ultraviolet laser energy to be transmitted through the laser catheter 22 to the target site. The laser pulse from diagnostic laser 10 stimulates fluorescence from noncalcified plaque and photoemission from calcified plaque. Fluorescence is detected by optical multichannel analyzer 42, and the spectral information is provided to computer 44. The computer 44 performs the fluorescence analysis algorithm in step 142. The calcium photoemission, if any, from the target site is transmitted through laser catheter 22 to detector 50. The output of detector 50 is analyzed by signal processor 53 as described above.

When the fluorescence analysis indicates the presence of noncalcified plaque in step 144, the ablation laser 12 is energized in step 146. When the fluorescence analysis is negative in step 144, but the analysis of calcium photoemission indicates the presence of calcified plaque in step 148, the ablation laser is energized in step 146. When the analysis is negative with respect to noncalcified plaque and calcified plaque, the procedure is terminated in step 150. When a defective catheter is identified in step 152 in response to the ablation laser being energized, the procedure is terminated in step 150. Although the ablation laser may be energized for a predetermined time or for a predetermined number of pulses, detection of a defective catheter causes an immediate termination of the procedure. When a defective catheter is not identified in step 152, the diagnostic laser 10 is again energized in step 140, and the analysis is repeated. The second embodiment of the angioplasty system provides the advantage that both fluorescence and calcium photoemission are stimulated by the diagnostic laser 10, and the ablation laser 10 is not energized until atherosclerotic plaque has been identified at the target site.

Figure 8:
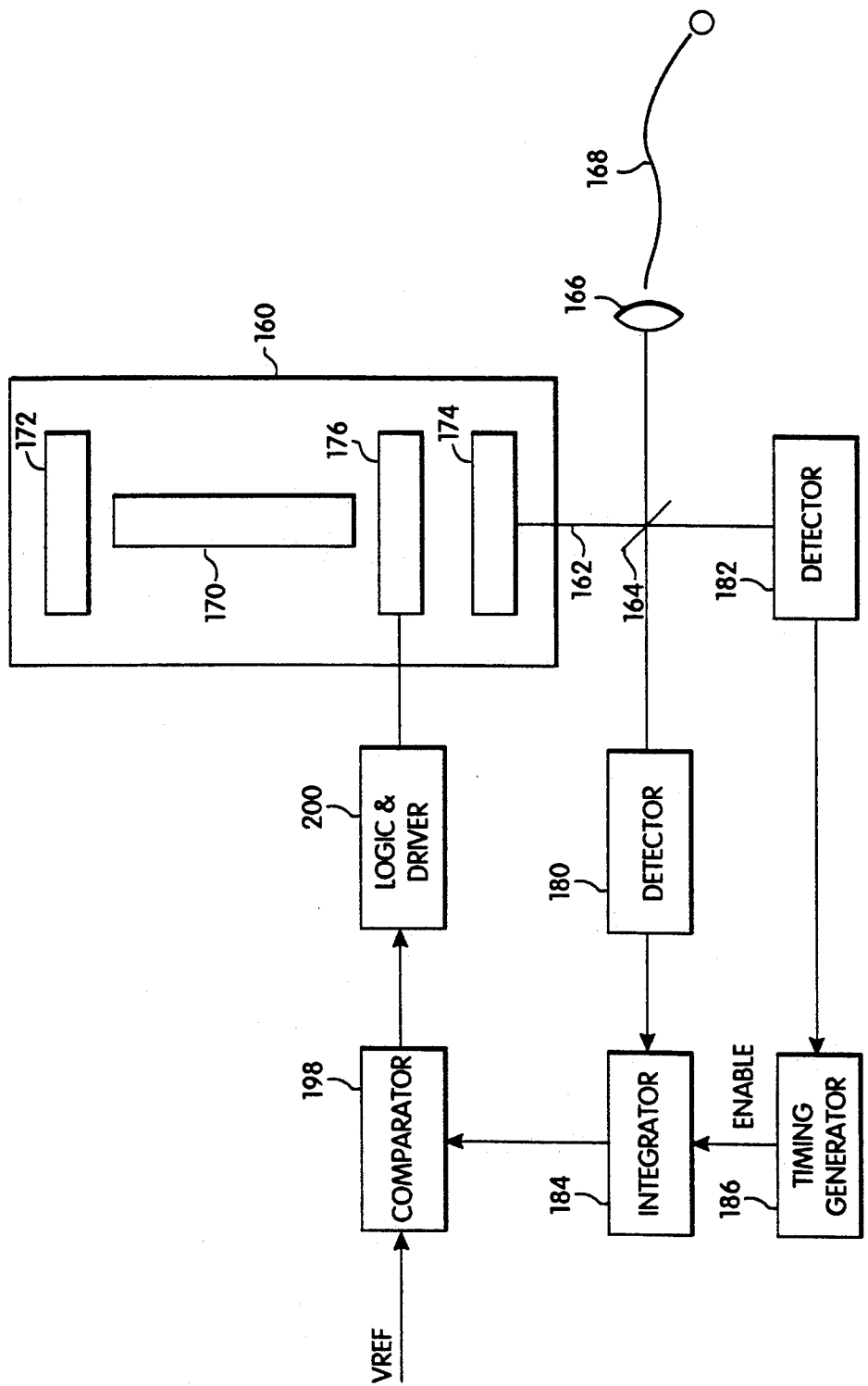
FIG. 8 is a schematic block diagram of a system for detection and ablation of calcified atherosclerotic plaque.

A block diagram of a system which utilizes an alternate technique for controlling ablation of calcified plaque is shown in FIG. 8. A laser 160 generates an output laser beam 162 which is directed by a beam splitter 164 through a lens 166 to the proximal end of a laser catheter 168. The laser catheter 168, which can be the same as the laser catheter 22 described above, directs laser energy to a target site in a blood vessel. The laser 160 is selected to stimulate calcium photoemission from calcified plaque at the target site and to cause ablation of tissue at the target site.

In general, the system of FIG. 8 operates by identifying the presence of calcified plaque at the target site during an initial, nonablative part of the laser ablation pulse. If the presence of calcified plaque at the target site is indicated, the laser pulse is completed. If the presence of calcified plaque is not indicated, the laser pulse is terminated prior to substantial ablation of tissue. Typically, the laser pulse is terminated in about 10 microseconds. A suitable laser 160 for implementation of the technique is a holmium-doped YAG laser having an output pulse width in the range of about 300-400 microseconds. Other lasers described above as suitable for ablation laser 12 can also be utilized. By terminating the laser pulse within about 10 microseconds when calcified plaque is not present, significant ablation is avoided. It will be understood that the technique is most useful for lasers which generate relatively wide pulse widths. For example, it would be difficult to analyze the calcium photoemission signal and terminate the ablation laser pulse in cases where the laser pulse width is on the order of 100 nanoseconds or less.

The laser 160 includes a rod 170 of active material such holmium-doped YAG, mirrors 172 and 174 at opposite ends of rod 170 and an acousto-optic switch 176 positioned between one of the mirrors and the rod 170. The acousto-optic switch 176 selectively interrupts the optical path between mirrors 172 and 174 in response to an electrical signal such that operation of the laser 160 is terminated when the switch 176 is off. The acousto-optic switch 176 provides extremely fast operation, typically on the order of 10-100 nanoseconds. A suitable acousto-optic switch 176 is a quartz substrate acousto-optic modulator, manufactured by Andersen Labs.

Calcium photoemission from the target site is directed through catheter 168 and through beam splitter 164 to a detector 180. The output of detector 180 is connected to the input of an integrator 184. A portion of the laser pulse generated by laser 160 is detected by a detector 182. The output of detector 182 is connected to a timing generator 186 which provides an enable signal to integrator 184.

Figure 9A:
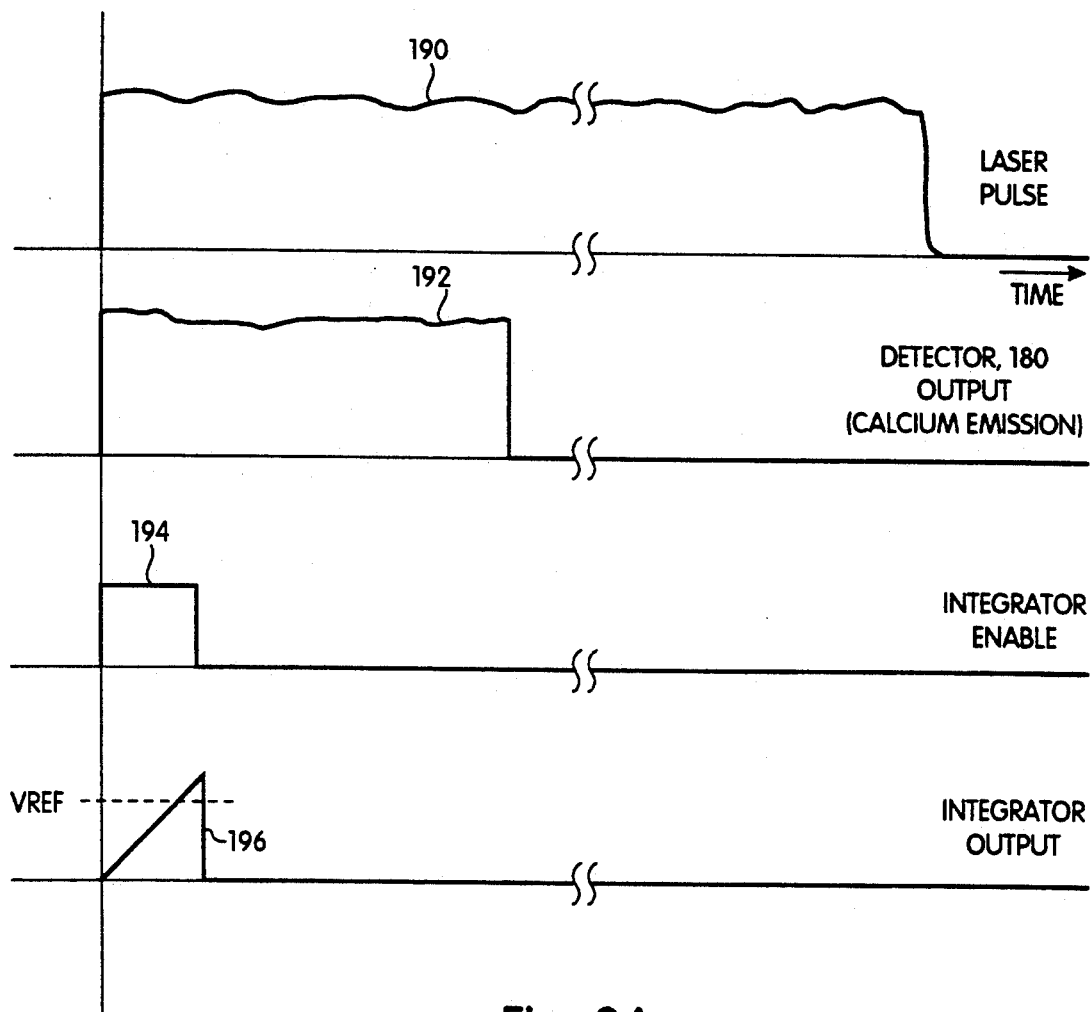
FIG. 9A is a timing diagram which illustrates operation of the system of FIG. 8 when calcified plaque is detected.
Figure 9B:
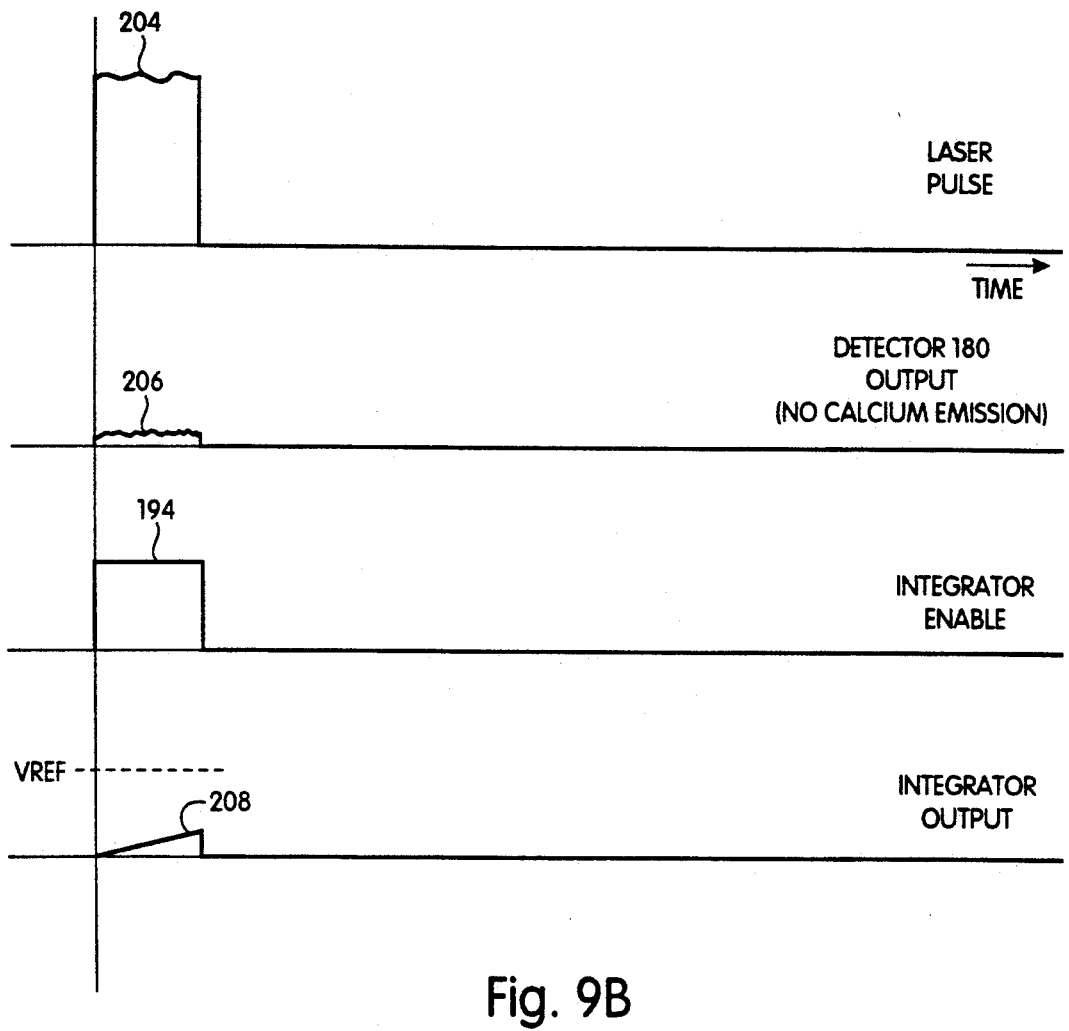
FIG. 9B is a timing diagram which illustrates operation of the system of FIG. 8 when calcified plaque is not detected.

Waveforms associated with the operation of the system of FIG. 8 are shown in FIGS. 9A and 9B. In the example of FIG. 9A, calcified plaque is present at the target site. A laser pulse 190 generated by laser 160 is directed to the target site. The calcium photoemission from the target site is detected by detector 180 as a signal 192. As discussed previously, the calcium emission signal has a relatively high intensity and a relatively short duration, on the order to 10-100 microseconds. The leading edge of the laser pulse 190 triggers the timing generator 186, which generates an integrator enable signal 194 having a duration on the order of about 10 microseconds. The output of integrator 184, as indicated by waveform 196, is connected to one input of a comparator 198. A reference voltage VREF is connected to the other input of comparator 198. The reference voltage VREF is selected such that the integrator output exceeds the reference voltage when calcified plaque is present at the target site. When the integrator output exceeds the reference voltage VREF, the comparator 198 provides an activation signal to a logic and driver unit 200. The logic and driver unit 200 includes a suitable drive circuit for operating acousto-optic switch 176. In addition, the unit 200 includes logic for controlling the acousto-optic switch 176 in response to the output of comparator 198. If the comparator 198 provides an activation signal during the integrator enable signal 194 (the first ten microseconds of the laser pulse), the logic and driver unit 200 maintains the acousto-optic switch 176 in the "on" state for the duration of the laser pulse 190, as shown in FIG. 9A.

A case in which no calcified plaque is present at the target site is illustrated in FIG. 9B. A laser pulse 204 is directed at the target site. In the absence of calcified plaque, a detected signal 206 from detector 180 is relatively low in amplitude. The integrator enable signal 194 enables integrator 184 for approximately 10 microseconds, causing an integrator output signal 208 to increase at a relatively slow rate. At the end of the integrator enable signal 194, the integrator output signal 208 does not exceed the reference voltage VREF, and comparator 198 does not provide an activation signal. At the end of the integrator enable signal 194, the logic and driver unit 200 determines that calcified plaque is not present at the target site, and acousto optic switch 176 is switched to the "off" state. As a result, the laser pulse 204 is terminated after approximately 10 microseconds, and no substantial ablation of the target site occurs.

The technique for controlling the ablation laser shown in FIGS. 8, 9A and 9B and described hereinabove can be employed in the embodiment of the angioplasty system of FIG. 1 in which the ablation laser 12 stimulates calcium photoemission from calcified plaque. The ablation laser 12 would be provided with an acousto-optic switch, and the signal processor 52 would generate a signal suitable for controlling the acousto-optic switch.

The analysis of time domain signals described above is performed by dedicated circuitry, and the outputs are supplied to computer 44. Alternatively, the time domain signals can be digitized, and the digitized values can be supplied to computer 44 for analysis. The computer 44 can perform any required analysis of the digitized time domain signals. For example, the computer 44 can determine the area under the time domain signal for a predetermined time interval and compare the area with a reference value to determine the presence of calcified plaque or a defective catheter condition.

The analysis of time domain signals representative of calcium photoemission is used in combination with fluorescence analysis in the system of FIG. 1 to insure that both noncalcified plaque and calcified plaque are identified and removed. When the identification and removal of noncalcified plaque are not required, the system elements that are dedicated to fluorescence analysis can be omitted. In the first embodiment of FIG. 1, the diagnostic laser 10 and the optical multichannel analyzer 42 can be omitted. In the second embodiment of FIG. 1, the diagnostic laser 10 must be retained since it is used for stimulating calcium photoemission. The analyzer 42 can be omitted. In both embodiments, the fluorescence analysis functions of computer 44 can be omitted. The analysis of time domain signals representative of calcium photoemission can be performed either with or without the detection of a defective catheter.

While there have been shown and described what are at present considered the preferred embodiments of the present invention, it will be obvious to those skilled in the art that various changes and modifications may be made therein without departing from the scope of the invention as defined by the appended claims.

What is claimed is:

1. An angioplasty method comprising the steps of:
   directing laser energy for stimulation of fluorescence by noncalcified atherosclerotic plaque and laser energy for stimulation of photoemission by calcified atherosclerotic plaque through a laser catheter to a target site in a blood vessel, the step of directing laser energy for stimulation of photoemission including directing a laser pulse through the laser catheter;
   analyzing a spectrum of the fluorescence emitted by tissue at the target site to determine whether the florescence is representative of noncalcified atherosclerotic plaque;
   analyzing photoemission by tissue at the target site to determine whether the photoemission is representative of calcified atherosclerotic plaque;
   directing high power laser energy through the laser catheter to the target site if the analyzing steps indicate the presence of atherosclerotic plaque; and
   detecting a defective condition of an optical fiber in said laser catheter by analyzing a tim domain signal responsive to photoemission received from the laser catheter and determining if the time domain signal is representative of a defective condition of said optical fiber, the step of analyzing a time domain signal including determining an area under the time domain signal beginning a predetermined time after the start of the laser pulse and indicating a defective condition of the optical fiber when said area exceeds a predetermined value.

2. An angioplasty method as defined in claim 1 wherein the step of analyzing photoemission includes analyzing a time domain signal responsive to photoemission by calcified atherosclerotic plaque at the target site.

3. An angioplasty method as defined in claim 2 wherein the step of analyzing a time domain signal includes determining the area under the time domain signal and indicating the presence of calcified atherosclerotic plaque when said area exceeds a predetermined value.

4. An angioplasty method comprising the steps of:
   directing a laser pulse for ablation of tissue and for stimulation of photoemission by calcified atherosclerotic plaque through a laser catheter to a target site in a blood vessel;
   analyzing a time domain signal responsive to photoemission by tissue at the target site to determine whether the photoemission is representative of calcified atherosclerotic plaque or tissue which does not contain atherosclerotic plaque; and
   terminating the laser pulse during an initial portion thereof if the time domain signal is not representative of calcified atherosclerotic plaque.

* * * * *